United States Patent [19]
Englert et al.

[11] Patent Number: 5,731,341
[45] Date of Patent: Mar. 24, 1998

[54] SUBSTITUTED BENZENESULFONYLUREAS AND -THIOUREAS, PREPARATION PROCESSES AND POSSIBLE USES OF PHARMACEUTICAL PREPARATIONS BASED ON THESE COMPOUNDS

[75] Inventors: Heinrich Englert, Hofheim; Dieter Mania, Königstein; Jens Hartung, Höchberg; Heinz Gögelein; Joachim Kaiser, both of Frankfurt; Uwe Gerlach, Hattersheim, all of Germany

[73] Assignee: Hoechst Aktiengesellschaft, Frankfurt am Main, Germany

[21] Appl. No.: 705,697

[22] Filed: Aug. 30, 1996

Related U.S. Application Data

[60] Division of Ser. No. 462,033, Jun. 5, 1995, Pat. No. 5,631,275, which is a continuation-in-part of Ser. No. 365,543, Dec. 28, 1994, abandoned.

Foreign Application Priority Data

Dec. 30, 1993 [DE] Germany ............................ 43 44 957.3

[51] Int. Cl.⁶ .................... A61K 31/40; C07D 209/46
[52] U.S. Cl. .................................... 514/416; 548/472
[58] Field of Search ........................... 548/472; 514/416

[56] References Cited

U.S. PATENT DOCUMENTS

| | | | |
|---|---|---|---|
| 4,379,785 | 4/1983 | Weyer et al. | 548/538 |
| 5,416,105 | 5/1995 | Satoh et al. | 514/423 |

FOREIGN PATENT DOCUMENTS 0 031 058  7/1981  European Pat. Off.

OTHER PUBLICATIONS

Fosset et al., "Identification, Mechanism of Function and Regulation of ATP–Sensitive Potassium Channels As Targets For Sulfonylureas Used in the Treatment of Type II Diabetes", Journ. Annu. Diabetol. Hotel–Dieu vol. 111, No. 21, Nov. 20, 1989. Chemical Abstract No. CA III:186728g.

*Primary Examiner*—Johann Richter
*Assistant Examiner*—Laura L. Stockton
*Attorney, Agent, or Firm*—Finnegan, Henderson, Farabow, Garrett & Dunner, L.L.P.

[57] ABSTRACT

Described herein are substituted benzenesulfonylureas and -thioureas of the formula (I):

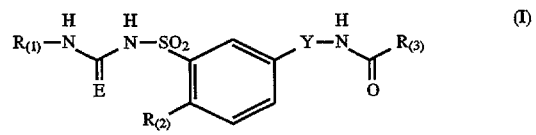

useful in treatment of disturbances in cardiac rhythm and prevention of sudden cardiac death caused by arrythmia. The compounds of formula (I) can be used as antiarrythmics and are particularly suitable for those cases where arrhythmias are a consequence of a narrowing of a coronary vessel, such as angina pectoris or acute cardiac infarction.

12 Claims, No Drawings

SUBSTITUTED BENZENESULFONYLUREAS AND -THIOUREAS, PREPARATION PROCESSES AND POSSIBLE USES OF PHARMACEUTICAL PREPARATIONS BASED ON THESE COMPOUNDS

This is a divisional application Ser. No. 08/462,033 filed Jun. 5, 1995, now U.S. Pat. No. 5,634,275 which is a continuation-in-part of application Ser. No. 08/365,543 filed Dec. 28, 1994 now abandoned.

The invention relates to substituted benzenesulfonylureas and -thioureas of the formula

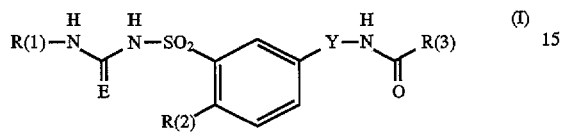

in which

R(1) is hydrogen, $(C_1-C_6)$-alkyl, $(C_3-C_6)$-cycloalkyl, $C_aH_{2a}$-$(C_3-C_5)$-cycloalkyl, $(C_3-C_6)$-alkenyl or $C_cH_{2c}$—$C_dF_{2d+1}$;

a is 0, 1, 2 or 3;

c is 0, 1, 2 or 3;

d is 1, 2, 3, 4, 5 or 6;

R(2) is hydrogen, F, Cl, Br, I, $(C_3-C_6)$-alkyl, $(C_1-C_6)$-alkoxy, $(C_1-C_6)$-mercaptoalkyl, $(C_1-C_6)$-fluoroalkoxy, O—$C_eH_{2e}$—$C_fF_{2f+1}$, $(C_1-C_6)$-fluoroalkyl, $C_gH_{2g}$—$C_hF_{2h+1}$, $(C_3-C_6$-cycloalkyl or NR(4)R(5);

e is 0, 1, 2 or 3;

f is 1, 2, 3, 4, 5 or 6;

g is 0, 1, 2 or 3;

h is 1, 2, 3, 4, 5 or 6;

R(4) and R(5) together are a $(CH_2)_{2-7}$ chain in which one of the $CH_2$ groups can be replaced by oxygen, sulfur or NR(6), where at least one $CH_2$ group must stand between the N atom of the NR(4)R(5) and the oxygen, sulfur or NR(6);

or

R(4), R(5) and R(6) independently of one another are hydrogen, $(C_1-C_6$-alkyl, $C_kH_{2k}$—$C_mF_{2m+1}$, $(C_3-C_6)$-cycloalkyl, $(C_1-C_2)$-alkyl-$(C_3-C_5)$-cycloalkyl or $(C_3-C_6)$-alkenyl;

k is 0, 1, 2 or 3;

m is 1, 2, 3, 4, 5 or 6;

E is oxygen or sulfur;

Y is a hydrocarbon chain —$[CR(7)_2]_n$

R(7) is H or $(C_1-C_2)$-alkyl;

n is 1, 2, 3 or 4;

R(3) is a substituted heterocyclic radical of the formula

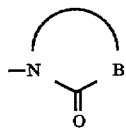

B is $(C_3-C_6)$-alkenyl, which is unsubstituted or substituted by up to 3 $(C_1-C_4)$-alkyl groups or by a phenyl radical;

or

R(3) is a bicyclic system of the formulae

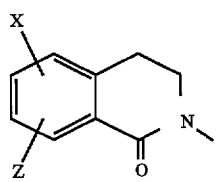

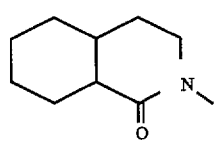

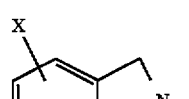

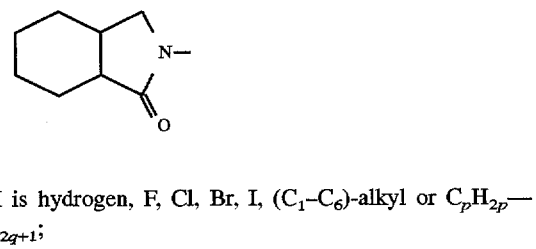

X is hydrogen, F, Cl, Br, I, $(C_1-C_6)$-alkyl or $C_pH_{2p}$—$C_qF_{2q+1}$;

p is 0, 1, 2 or 3;

q is 0, 1, 2, 3, 4, 5 or 6;

Z is F, Cl, Br, I, $(C_1-C_4)$-alkoxy, $(C_1-C_4)$-alkyl, $(C_3-C_6)$-cycloalkyl or $(C_3-C_6)$-cycloalkoxy.

Preferred compounds of the formula I are those in which:

R(1) is hydrogen, $(C_1-C_4)$-alkyl, $(C_3-C_5)$-cycloalkyl, $(C_3-C_5)$-alkenyl or $C_cH_{2c}$—$C_dF_{2d+1}$;

c is 0, 1, 2 or 3;

d is 1, 2, 3, 4, 5 or 6;

R(2) is hydrogen, F, Cl, $(C_1-C_6)$-alkyl, $(C_1-C_6)$-alkoxy, $(C_1-C_6)$-mercaptoalkyl, $(C_1-C_6)$-fluoroalkoxy, $(C_1-C_6)$-fluoroalkyl, $(C_3-C_6)$-cycloalkyl or NR(4)R(5);

R(4) and R(5)
together are a $(CH_2)_{2-7}$ chain, in which one of the $CH_2$ groups can be replaced by oxygen, sulfur or NR(6), where at least one $CH_2$ group must stand between the N atom of the NR(4)R(5) and the oxygen, sulfur or NR(6);

or

R(4), R(5) and R(6) independently of one another are hydrogen, $(C_1-C_6)$-alkyl, $C_kH_{2k}$—$C_mF_{2m+1}$, $C_3-C_6$-cycloalkyl, $(C_1-C_2)$-alkyl-$(C_3-C_5)$-cycloalkyl or $(C_3-C_6)$-alkenyl;

k is 0, 1 or 2;

m is 1, 2, 3, 4, 5 or 6;

E is oxygen or sulfur;

Y is a hydrocarbon chain —$[CR(7)_2]_n$—;

R(7) is H or $(C_1-C_2)$-alkyl;

n is 1, 2, 3 or 4;

R(3) is a substituted heterocyclic radical of the formula

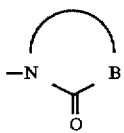

B is $(C_3-C_6)$-alkenyl,
  which is unsubstituted or substituted by up to 3 $(C_1-C_4)$-alkyl groups or by a phenyl radical;
or
R(3) is a bicyclic system of the formulae

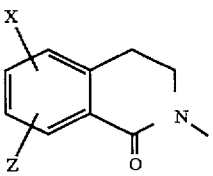

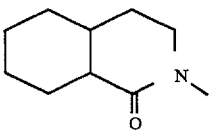

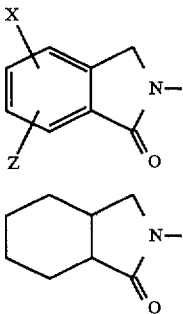

X is hydrogen, F, Cl, Br, I or $(C_1-C_6)$-alkyl;
Z is F, Cl, Br, I, $(C_1-C_4)$-alkoxy, $(C_1-C_4)$-alkyl, $(C_3-C_6)$-cycloalkyl or $(C_3-C_6)$-cycloalkoxy.

Particularly preferred compounds of the formula 1 are those in which:
R(1) is hydrogen, $(C_1-C_4)$-alkyl, $(C_3-C_4)$-cycloalkyl, $(C_3-C_4)$-alkenyl or $(C_1-C_4)$-fluoroalkyl;
R(2) is hydrogen, F, Cl, $(C_1-C_4)$-alkyl, $(C_1-C_4)$-fluoroalkyl or $(C_3-C_6)$-cycloalkyl;
E is oxygen or sulfur;
Y is a hydrocarbon chain '$[CR(7)_2]_n$—;
R(7) is H or $(C_1-C_2)$-alkyl;
n is 2 or 3;
R(3) is a substituted heterocyclic radical of the formula

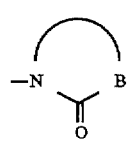

B is $(C_3-C_6)$-alkenyl, which is unsubstituted or substituted by up to 3 $(C_1-C_4)$-alkyl groups or by a phenyl radical;
or R(3) is a bicyclic system of the formulae

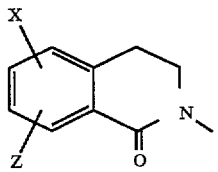

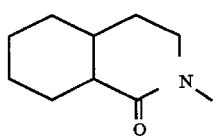

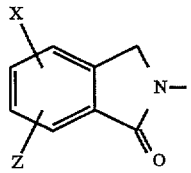

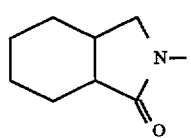

X is hydrogen, F, Cl or $(C_1-C_3)$-alkyl;
Z is F, Cl or $(C_1-C_4)$-alkoxy.

Compounds of the formula I which are likewise particularly preferred are those in which:
R(1) is hydrogen, $(C_1-C_4)$-alkyl, $(C_3-C_4)$-cycloalkyl, $(C_3-C_4)$-alkenyl or $(C_1-C_4)$-fluoroalkyl;
R(2) is $(C_1-C_4)$-alkoxy, $(C_1-C_4)$-mercaptoalkyl or $(C_1-C_4)$-fluoroalkoxy;
E is oxygen or sulfur;
Y is a hydrocarbon chain —$[CR(7)_2]_n$—;
R(7) is H or $(C_1-C_2)$-alkyl;
n is 2 or 3;
R(3) is a substituted heterocyclic radical of the formula

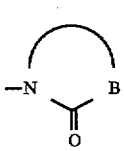

B is $(C_3-C_4)$-alkenyl,
  which is unsubstituted or substituted by one to three $(C_1-C_4)$-alkyl groups or by a phenyl radical;
or
R(3) is a bicyclic system of the formulae

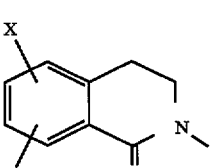

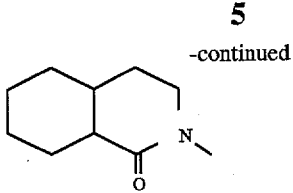

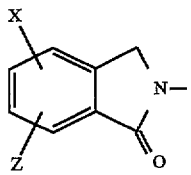

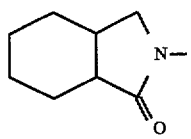

X is hydrogen, F, Cl or (C$_1$–C$_3$)-alkyl;
Z is F, Cl or (C$_1$–C$_4$)-alkoxy.

Compounds of the formula I which are likewise especially preferred are those in which R(1) is hydrogen, (C$_1$–C$_4$)-alkyl, (C$_3$–C$_4$)-alkenyl or (C$_1$–C$_4$)-fluoroalkyl;

R(2) is NR(4)R(5);

R(4) and R(5)
  together are a (CH$_2$)$_{4-6}$ chain, in which one of the CH$_2$ groups can be replaced by oxygen, sulfur or NR(6), where at least one CH$_2$ group must stand between the N atom of the NR(4)R(5) and the oxygen, sulfur or NR(6);

or

R(4) and R(5) independently of one another are CH$_3$, C$_2$H$_5$, n-C$_3$H$_7$, iso-C$_3$H$_7$ or cyclo-C$_3$H$_5$;

R(6) is H, CH$_3$ or C$_2$H$_5$;

E is oxygen or sulfur;

Y is a hydrocarbon chain —[CR(7)$_2$]$_n$—;

R(7) is H or (C$_1$–C$_2$)-alkyl;

n is 2 or 3;

R(3) is a substituted heterocyclic radical of the formula

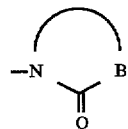

B is (C$_3$–C$_4$)-alkenyl,
  which is unsubstituted or substituted by up to 3 (C$_1$–C$_4$)-alkyl groups or by a phenyl radical;

or

R(3) is a bicyclic system of the formulae

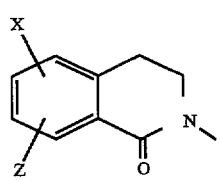

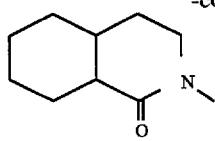

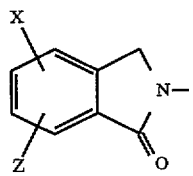

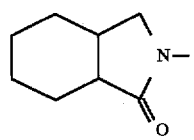

X is hydrogen, F, Cl or (C$_1$–C$_3$)-alkyl;
Z is F, Cl or (C$_1$–C$_4$)-alkoxy.

Particularly preferred are also compounds of the formula I in which

R(1) is hydrogen, (C$_1$–C$_2$)-alkyl, CF$_3$, C$_2$F$_5$ or CH$_2$CF$_3$;

R(2) is Cl, (C$_1$–C$_6$)-alkyl, (C$_1$–C$_6$)-alkoxy, (C$_1$–C$_6$)-mercaptoalkyl, (C$_1$–C$_6$)-fluoroalkoxy, (C$_1$–C$_6$)-fluoroalkyl, (C$_3$–C$_6$)-cycloalkyl or NR(4)R(5); R(4) and R(5)

together are a (CH$_2$)$_{2-7}$ chain, in which one of the CH$_2$ groups can be replaced by oxygen, sulfur or NR(6), where at least on a CH$_2$ group must stand between the N atom of the NR(4)R(5) and the oxygen, sulfur or NR(6);

or

R(4), R(5) and R(6) independently of one another are hydrogen, (C$_1$–C$_6$)-alkyl, C$_k$H$_{2k}$—C$_m$F$_{2m+1}$, (C$_3$C$_6$)-cycloalkyl, (C$_1$–C$_2$)-alkyl-(C$_3$–C$_5$)-cycloalkyl or (C$_3$–C$_6$)-alkenyl;

k is 0, 1 or 2;

m is 1, 2, 3, 4, 5 or 6;

E is oxygen or sulfur;

Y is a hydrocarbon chain —[CR(7)$_2$]$_n$—;

R(7) is H or (C$_1$–C$_2$)-alkyl;

n is 1, 2, 3 or 4;

R(3) is a substituted heterocyclic radical of the formula

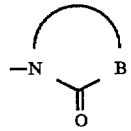

B is (C$_3$–C$_6$)-alkenyl,
  which is unsubstituted or substituted by up to 3 (C$_1$–C$_4$)-alkyl groups or by a phenol radical;

or

R(3) is a bicyclic system of the formulae

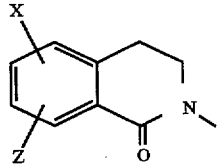

-continued

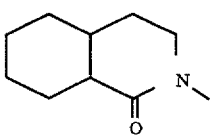

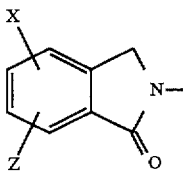

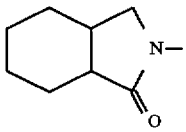

X is hydrogen, F, Cl, Br, I or $(C_{C1}-C_6)$-alkyl;

Z is F, Cl, Br, I, $(C_1-C_4)$-alkoxy, $(C_1-C_4)$-alkyl, $(C_3-C_6)$-cycloalkyl or $(C_3-C_6)$-cycloalkoxy.

Likewise especially preferred are also compounds of the formula I in which

R(1) is hydrogen or methyl;

R(2) is $(C_1-C_3)$-alkyl, $(C_1-C_6)$-alkoxy, $(C_1-C_6)$-mercaptoalkyl, $(C_1-C_6)$-fluoroalkoxy, $(C_1-C_3)$-fluoroalkyl or $(C_3-C_6)$-cycloalkyl;

E is oxygen or sulfur;

Y is a hydrocarbon chain $—[CR(7)_2]_n—$;

R(7) is H or $(C_1-C_2)$-alkyl;

n is 1, 2, 3 or 4;

R(3) is a substituted heterocyclic radical of the formula

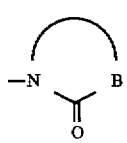

B is $(C_3-C_6)$-alkenyl, which is unsubstituted or substituted by up to 3 $(C_1-C_4)$-alkyl groups or by a phenyl radical;

or

R(3) is a bicyclic system of the formulae

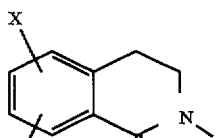

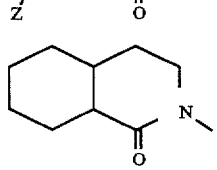

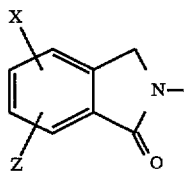

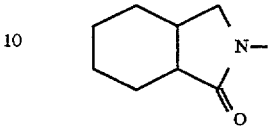

X is hydrogen, F, Cl, Br, I or $(C_1-C_6)$-alkyl;

Z is F, Cl, Br, I, $(C_1-C_4)$-alkoxy, $(C_1-C_4)$-alkyl, $(C_3-C_6)$-cycloalkyl or $(C_3-C_6)$-cycloalkoxy.

Unless stated otherwise, the term alkyl describes straight-chain or branched saturated hydrocarbon radicals. The cycloalkyl radical can additionally carry an alkyl substituent.

Unless expressly stated otherwise, fluoroalkyl and fluoroalkoxy are a straight-chain or branched saturated alkyl or alkoxy radical having 1 to 6 carbon atoms, in which at least one or not more than all the hydrogens are replaced by fluorine.

Compounds having centers of chirality in the alkyl side chain Y furthermore may occur. In this case, both the individual antipodes in themselves and a mixture of the two enantiomers in various ratios, as well as the associated meso compounds or mixtures of meso compounds, the enantiomers or diastereomers, belong to the invention.

Similar sulfonylureas are known from German Offenlegungsschrift 2 413 514, German Patent 1 518 874 and European Patent 0,031,058. DE-OS 2 413 514 and EP 0,031,058 describe exclusively blood sugar-conditioning substances with p-substitution in the central phenyl group. There are no references to m-substitution.

The hypoglycemic effects of sulfonylureas are described in the patent publications. The prototype of such hypoglycemic sulfonylureas is glibenclamide, which is used therapeutically as an agent for the treatment of diabetes mellitus and is used in science as a much-regarded tool for researching so-called ATP-sensitive potassium channels. In addition to its hypoglycemic action, glibenclamide also has other actions which it has so far not yet been possible to employ therapeutically but which are all attributed to blockade precisely of these ATP-sensitive potassium channels. These include, in particular, an antifibrillatory action on the heart. However, simultaneous lowering of blood sugar would be undesirable or even dangerous during treatment of ventricular fibrillation or its preliminary stages, since it may deteriorate the condition of the patient further.

The object of the present invention was therefore to synthesize compounds which have a cardiac action which is equally as good as that of glibenclamide, but do not influence, or influence to a significantly lesser degree than glibenclamide, the blood sugar in cardioactive doses or concentrations.

Suitable test animals for detection of such actions are, for example, mice, rats, guineapigs, rabbits, dogs, monkeys or pigs.

The compounds I are used as medicament active compounds in human and veterinary medicine. They can furthermore be used as intermediate products for the preparation of other medicament active compounds.

The compounds I of the present invention are useful medicaments for the treatment of disturbances in cardiac rhythm of widely varying origin and for prevention of sudden cardiac death caused by arrhythmia, and can therefore be used as antiarrhythmics. Examples of arrhythmic disturbances of the heart are supraventricular disturbances in rhythm, such as, for example, auricular tachycardia, auricular flutter or paroxysmal supraventricular disturbances in rhythm, or ventricular disturbances in rhythm, such as ventricular extrasystoles, but in particular life-threatening ventricular tachycardias or the particularly dangerous ventricular fibrillation. They are particularly suitable for those cases where arrhythmias are a consequence of a narrowing of a coronary vessel, such as occur, for example, with angina pectoris or during an acute cardiac infarction or as a chronic consequence of a cardiac infarction. They are therefore particularly suitable for prevention of sudden cardiac death in post-infarction patients. Other syndromes in which such disturbances in rhythm and/or sudden cardiac death caused by arrhythmia play a role are, for example, cardiac insufficiency or cardiac hypertrophy as a consequence of a chronically increased blood pressure.

The compounds I furthermore can positively influence a reduced contractility of the heart. This can be a disease-related decrease in cardiac contractility, for example in cases of cardiac insufficiency, or acute cases, such as cardiac failure under the effects of shock. In cases of a heart transplant, the heart likewise can resume its efficiency faster and more reliably after the operation has been performed. The same applies to operations on the heart which necessitate temporary stopping of cardiac activity by cardioplegic solutions, it being possible for the compounds to be used both for protection of the organs, for example during treatment with or storage thereof in physiological bath liquids, and during transfer into the recipient organism.

The invention furthermore relates to a process for the preparation of the compounds I, which comprises (a) reacting sulfonamides of the formula II or salts thereof of the formula III with R(1)-substituted isocyanates of the formula IV

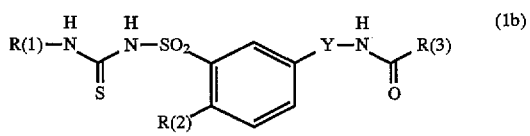

R(1)—N=C=O            IV to give substituted benzenesulfonylureas Ia.

Possible cations M in the salts of the formula III are alkali metal and alkaline earth metal ions, in particular Na⁺, K⁺, Ca⁺⁺ and Mg⁺⁺. As equivalent to the R(1)-substituted isocyanates IV, R(1)-substituted carbamic acid esters, R(1)-substituted carbamic acid halides or substituted ureas can be employed.

(b) Benzenesulfonylureas Ia

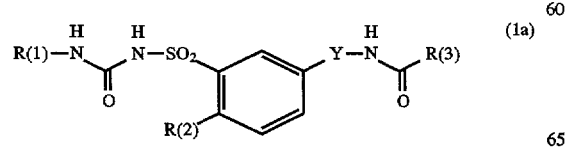

can be prepared from aromatic benzenesulfonamides II or their salts III and R(1)-substituted trichloroacetides of the formula V

in the presence of a base in an inert solvent according to Synthesis 1987, 734–735 at temperatures of 25° C. to 150° C.

Suitable bases are, for example, alkali metal or alkaline earth metal hydroxides, or also alcoholates, such as sodium hydroxide, potassium hydroxide, calcium hydroxide, sodium methylate, sodium ethanolate, potassium methylate or potassium ethanolate. Suitable inert solvents are ethers, such as tetrahydrofuran, dioxane and ethylene glycol dimethyl ether (diglyme), nitriles, such as acetonitrile, amides, such as dimethylformamide (DMF) or N-methylpyrrolidone (NMP), phosphoric acid hexamethyltriamide, sulfoxides, such as dimethyl sulfoxide, sulfones, such as sulfolane, and hydrocarbons, such as benzene, toluene and xylenes. Furthermore, mixtures of these solvents with one another are also suitable.

(c) Benzenesulfonylthioureas Ib

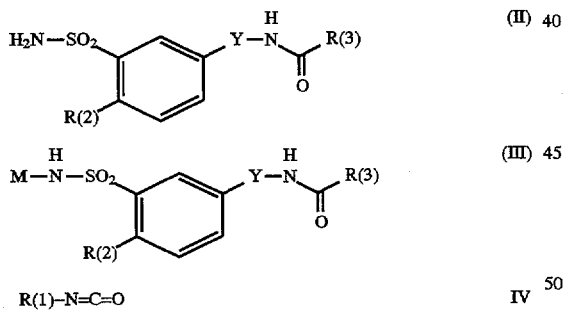

are prepared from benzenesulfonamides II and their salts III and R(1)-substituted thioisocyanates VI

R(1)—N=C=S            VI (d) Substituted benzenesulfonylureas of the formula Ia can be prepared by conversion reactions of benzenesulfonylthioureas of the structure Ib. The replacement of the sulfur atom by an oxygen atom in the correspondingly substituted benzenesulfonylthioureas Ib can be carried out, for example, with the aid of oxides or salts of heavy metals or also by using oxidizing agents, such as hydrogen peroxide, sodium peroxide or nitric acid. Thioureas can also be desulfurized by treatment with phosgene or phosphorus pentachloride. Chloroformic acid amidines or carbodiimides are obtained as intermediate compounds, which can be converted into the corresponding substituted benzenesulfonylureas Ia, for example, by hydrolysis or adding on of water. During desulfurization, isothioureas behave like thioureas and can accordingly likewise be used as starting substances for these reactions.

(e) Benzenesulfonylureas Ia can be prepared by reactions of amines of the formula R(1)-NH₂ with benzenesulfonyl isocyanates of the formula VII

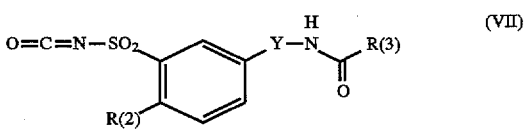

Amines R(1)-NH₂ can likewise be reacted with benzenesulfonylcarbamic acid esters or -carbamic acid halides or benzenesulfonylureas Ia (where R(1)=H) to give the compounds Ia.

(f) Benzenesulfonylthioureas Ib can be prepared by reactions of amines of the formula R(1)-NH₂ with benzenesulfonylisothiocyanates of the formula VIII

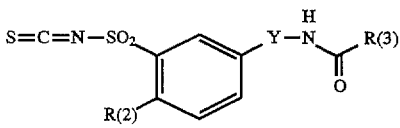

Amines R(1)-NH$_2$ likewise can be reacted with benzenesulfonylcarbamic acid thioesters of -carbamic acid thiohalides to give the compounds Ib.

The compounds I and physiologically acceptable salts thereof are useful therapeutics which are suitable not only as antiarrhythmics but also as prophylactics for disturbances of the cardiovascular system, cardiac insufficiency, heart transplant or cerebral vascular diseases in humans or mammals (for example monkeys, dogs, mice, rats, rabbits, guineapigs and cats).

Physiologically acceptable salts of the compounds I are understood as meaning, in accordance with Remmington's Pharmaceutical Science, 17th edition, 1985, pages 14–18, compounds of the formula IX

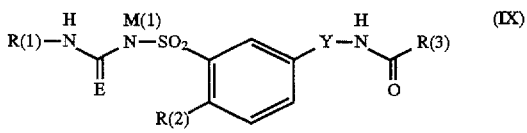

which can be prepared from non-toxic organic and inorganic bases and benzenesulfonylureas I.

Preferred salts here are those in which M(1) in the formula IX is sodium, potassium, rubidium, calcium or magnesium ions, and the acid addition products are basic amino acids, such as, for example, lysine or arginine.

The starting compounds for the synthesis processes mentioned for the benzenesulfonylureas I are prepared by methods which are known per se, such as are described in the literature (for example in the standard works, such as Houben-Weyl, Methoden der Organischen Chemie (Methods of Organic Chemistry), Georg Thieme Verlag, Stuttgart; Organic Reactions, John Wiley & Sons, Inc., New York; and in the abovementioned patent applications), end in particular under reaction conditions which are known and suitable for the reactions mentioned. It is also possible to use variants which are known per se but are not mentioned in more detail here. If desired, the starting substances can also be formed in situ such that they are not isolated from the reaction mixture but are immediately reacted further.

The amine X is first converted into an isocyanate or a reactive carbonic acid derivative (equation 1). The conversion of the amine X into an isocyanate is carried out in a known manner by reaction of X with carbonic acid halides, such as phosgene or triphosgene, in the presence of tertiary alkylamines or pyridine and inert solvents. Suitable inert solvents are ethers, such as tetrahydrofuran, dioxane or ethyleneglycoldimethyl ether (diglyme), ketones, such as acetone or butanone, nitriles, such as acetonitrile, nitro compounds, such as nitromethane, esters, such as ethyl acetate, amides, such as dimethylformamide (DMF) or N-methylpyrrolidone (NMP), phosphoric acid hexamethyltriamide, sulfoxides, such as dimethylsulfoxide, sulfones, such as sulfolane, and hydrocarbons, such as benzene, toluene and xylenes. Mixtures of these solvents with one another furthermore are suitable. Suitable reactive carbonic acid derivatives are carbonic acid esters such as can be synthesized from chloroformic acid alkyl esters and X and suitable tertiary alkylamines or pyridine. N,N-carbonyldiimidazole and analogous reactive derivatives furthermore can be employed as isocyanate equivalents (Staab, H. A.: Synthesen mit heterocyclischen Amiden (Azoliden) [Syntheses with heterocyclic amides (azolides)]. In: Angewandte Chemie 74 (1962), No. 12, pages 407–423).

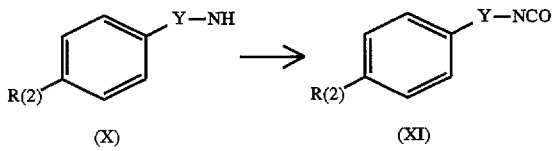

Equation 1

The isocyanate XI or corresponding urethanes are linked to the second molecular component (Justis Liebigs Ann. chem. 1956, 598, page 203) in the presence or absence of inert solvents at temperatures of 100°–170° C. and give the acylurea derivatives XII (equation 2)

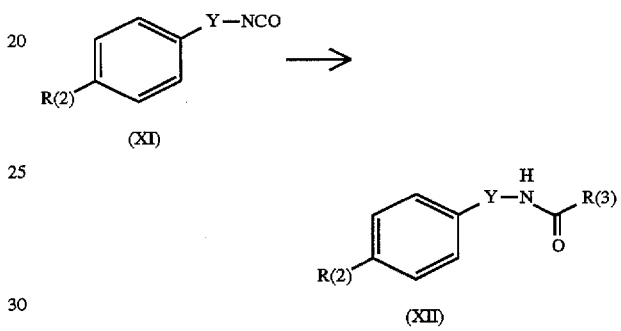

Equation 2

The compounds XII synthesized according to equation 2 can be converted into the sulfonamides II in a known manner in accordance with equation 3. The sulfonamides II are prepared by methods which are known per se, and in particular under reaction conditions which are known and suitable for the reactions mentioned. In this context, use can also be made of variants which are known per se but are not mentioned in more detail here. If desired, the syntheses can be completed in one, two or more steps. Processes in which the acylurea derivative XII is converted into aromatic sulfonic acids and derivatives thereof, such as, for example, sulfonic acid halides, by electrophilic reagents in the presence or absence of inert solvents at temperatures between −10° C. and 120° C., preferably between 0° C. and 100° C., are particularly preferred. For example, halogenosulfonations can be carried out with halogenosulfonic acids. Ortho and meta isomers can be formed in this reaction, end can be separated from one another at the next sulfonamide reaction stage by standard processes (for example column chromatography on inert support materials or crystallization from inert solvents). The conversion of the sulfonic acid derivatives into sulfonamides II is carried out in a manner known from the literature, sulfonic acid chlorides preferably being reacted with aqueous ammonia in inert solvents at temperatures of 0° C. to 100° C.

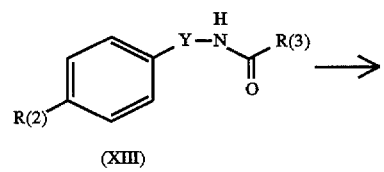

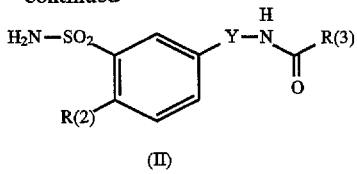

(II)

Equation 3

The benzenesulfonylureas of the formula I are prepared as mentioned above from the sulfonamide-substituted acylurea derivatives II thus prepared or acid addition compounds thereof. Depending on the nature of the members R(1), R(2), R(3), E, B, X, Y and Z, one or other of the processes mentioned will be unsuitable for the preparation of compounds I, or at least necessitate measures for protection of active groups, in individual cases. Such cases, which occur relatively rarely, can be recognized easily by the expert, and there are no difficulties in successfully using one of the other synthesis routes described in such cases.

The compounds I can possess one or more chiral centers. They can therefore be obtained in their preparation as racemetes or, if optically active starting substances are used, also in optically active form. If the compounds contain two or more chiral centers, they can be obtained in the synthesis as mixtures of racemetes, from which the individual isomers can be isolated in the pure form, for example by recrystallization from inert solvents. If desired, resulting racemates can be separated mechanically or chemically into their enantiomers by methods which are known per se. Thus, diastereomers can be formed from the racemate by reaction with an optically active separating agent. Suitable separating agents for basic compounds are, for example, optically active acids, such as the R or R,R and S or S,S forms of tartaric acid, dibenzoyltartaric acid, diacetyltartaric acid, camphor-sulfonic acid, mandelic acid, malic acid or lactic acid. Carbinols furthermore can be amidated with the aid of chiral acylating reagents, for example R- or S-α-methylbenzyl isocyanate, and then separated. The various forms of diastereomers can be separated in a known manner, for example by fractional crystallization, and the enantiomers of the formula I can be liberated in a manner which is known per se from the diastereomers. Enantiomer separations are also achieved by chromatography over optically active support materials.

The compounds I according to the invention and their physiologically acceptable salts can be used for the preparation of pharmaceutical formulations. In this context, they can be brought into a suitable dosage together with at least one solid or liquid excipient or auxiliary, by themselves or in combination with other cardiovascular medicaments, such as, for example, calcium antagonists, NO donors or ACE inhibitors. These formulations can be used as medicaments in human or veterinary medicine. Possible excipients are organic or inorganic substances which are suitable for enteral (for example oral), parenteral, such as, for example, intravenous, administration or topical applications and with which the novel compounds do not react, for example water, vegetable oils, benzyl alcohols, polyethylene glycols, glycerol triacetate, gelatin, carbohydrates, such as lactose or starch, magnesium stearate, talc, lanolin and vaseline. Tablets, coated tablets, capsules, syrups, juices or drops are suitable in particular for oral use, solutions, preferably oily or aqueous solutions, and furthermore suspensions, emulsions or implants are suitable for rectal use, and ointments, creams, pastes, lotions, gels, sprays, foams, aerosols, solutions (for example in alcohols, such as ethanol or isopropanol, 1,2-propanediol or mixtures thereof with one another or with water) or powders are suitable for topical use. The novel compounds can also be lyophilized and the resulting lyophilizates can be used, for example, for the preparation of injection preparations. Liposomal preparations are also possible, in particular, for topical use. The [lacuna] comprise stabilizers and/or wetting agents, emulsifiers, salts and/or auxiliaries, such as lubricants, preservatives, stabilizers and/or wetting agents, emulsifiers, salts for influencing the osmotic pressure, buffer substances, dyestuffs and flavor and/or aroma substances. If desired, they can also comprise one or more other active compounds, for example one or more vitamins.

The dosages which are necessary for treatment of disturbances in cardiac rhythm using the compounds I depend on whether therapy is acute or prophylactic. A dose range of at least about 0.001 mg, preferably about 0.01 mg, in particular about 0.1 mg to not more than about 100 mg, preferably about 10 mg, in particular about 1 mg per kg per day is usually adequate if prophylaxis is carried out. A dose range of 1 to 10 mg per kg and day is preferred. The dose here can be an oral or parenteral individual dose or divided into up to four individual doses. If acute cases of disturbances in cardiac rhythm are treated, for example in an intensive care ward, parenteral administration may be advantageous. A preferred dose range in critical situations can then be 10 to 100 mg, and can be administered, for example, as a continuous intravenous infusion.

In addition to the examples described in the embodiment examples, the compounds I summarized in the following table can be obtained according to the invention:

3-Ethyl-4-methyl-2-oxo-3-pyrrolinyl-1-carboxamides:

(1) 1-{2-Methoxy-5-[2-(3-ethyl-4-methyl-2-oxo-3-pyrrolinyl-1-carboxamido)-ethyl]-phenylsulfonyl-}3-ethylurea, (2) 1-{2-Methoxy-5-[2-(3-ethyl-4-methyl-2-oxo-3-pyrrolinyl-1-carboxamido)-ethyl]-phenylsulfonyl-}3-(1-propyl)-urea, (3) 1-{2-Methoxy-5-[2-(3-ethyl-4-methyl-2-oxo-3-pyrrolinyl-1-carboxamido)-ethyl]-phenylsulfonyl-}3-(2-propyl)-urea, (4) 1-{2-Methoxy-5-[2-(3-ethyl-4-methyl-2-oxo-3-pyrrolinyl-1-carboxamido)-ethyl]-phenylsulfonyl-}3-(cyclopropyl)-urea (5) 1-{2-Ethoxy-5-[2-(3-ethyl-4-methyl-2-oxo-3-pyrrolinyl-1-carboxamido)-ethyl]-phenylsulfonyl-}3-ethylurea, (6) 1-{2-Ethoxy-5-[2-(3-ethyl-4-methyl-2-oxo-3-pyrrolinyl-1-carboxamido)-ethyl]-phenylsulfonyl-}3-(1-propyl)-urea, (7) 1-{2-Ethoxy-5-[2-(3-ethyl-4-methyl-2-oxo-3-pyrrolinyl-1-carboxamido)-ethyl]-phenylsulfonyl-}3-(2-propyl)-urea, (8) 1-{2-Ethoxy-5-[2-(3-ethyl-4-methyl-2-oxo-3-pyrrolinyl-1-carboxamido)-ethyl]-phenylsulfonyl-}3-(cyclopropyl)-urea, (9) 1-{2-(2,2,2-Trifluoroethoxy)-5-[2-(3-ethyl-4-methyl-2-oxo-3-pyrrolinyl-1-carboxamido)-ethyl]-phenylsulfonyl-}3-ethylurea,

(10) 1-{2-(2,2,2-Trifluoroethoxy)-5-[2-(3-ethyl-4-methyl-2-oxo-3-pyrrolinyl-1-carboxamido)-ethyl]-phenylsulfonyl-}3-(1-propyl)-urea,

(11) 1-{2-(2,2,2-Trifluoroethoxy)-5-[2-(3-ethyl-4-methyl-2-oxo-3-pyrrolinyl-1-carboxamido)-ethyl]-phenylsulfonyl-}3-(2-propyl)-urea,

(12) 1-{2-(2,2,2-Trifluoroethoxy)-5-[2-(3-ethyl-4-methyl-2-oxo-3-pyrrolinyl-1-carboxamido)-ethyl]-phenylsulfonyl-}3-(cyclopropyl)-urea,

(13) 1-{2-Thiomethyl-5-[2-(3-ethyl-4-methyl-2-oxo-3-pyrrolinyl-1-carboxamido)-ethyl]-phenylsulfonyl-}3-ethylurea,

(14) 1-{2-Thiomethyl-5-[2-(3-ethyl-4-methyl-2-oxo-3-pyrrolinyl-1-carboxamido)-ethyl]-phenylsulfonyl-}3-(1-propyl)-urea,

(15) 1-{2-Thiomethyl-5-[2-(3-ethyl-4-methyl-2-oxo-3-pyrrolinyl-1-carboxamido)-ethyl]-phenylsulfonyl-}3-(2-propyl)-urea,

(16) 1-{2-Thiomethyl-5-[2-(3-ethyl-4-methyl-2-oxo-3-pyrrolinyl-1-carboxamido)-ethyl]-phenylsulfonyl-}3-(cyclopropyl)-urea,

(17) 1-{2-(N,N-Dimethylamino)-5-[2-(3-ethyl-4-methyl-2-oxo-3-pyrrolinyl-1-carboxamido)-ethyl]-phenylsulfonyl-}3-ethylurea,

(18) 1-{2-(N,N-Dimethylamino)-5-[2-(3-ethyl-4-methyl-2-oxo-3-pyrrolinyl-1-carboxamido)-ethyl]-phenylsulfonyl-}3-(1-propyl)-urea,

(19) 1-{2-(N,N-Dimethylamino)-5-[2-(3-ethyl-4-methyl-2-oxo-3-pyrrolinyl-1-carboxamido)-ethyl]-phenylsulfonyl-}3-(2-propyl)-urea,

(20) 1-{2-(N,N-Dimethylamino)-5-[2-(3-ethyl-4-methyl-2-oxo-3-pyrrolinyl-1-carboxamido)-ethyl]-phenylsulfonyl-}3-(cyclopropyl)-urea,

(21) 1-{2-(4-Morpholino)-5-[2-(3-ethyl-4-methyl-2-oxo-3-pyrrolinyl-1-carboxamido)-ethyl]-phenylsulfonyl-}3-ethylurea,

(22) 1-{2-(4-Morpholino)-5-[2-(B-ethyl-4-methyl-2-oxo-3-pyrrolinyl-1-carboxamido)-ethyl]-phenylsulfonyl-}3-(1-propyl)-urea,

(23) 1-{2-(4-Morpholino)-5-[2-(3-ethyl-4-methyl-2-oxo-3-pyrrolinyl-1-carboxamido)-ethyl]-phenylsulfonyl-}3-(2-propyl)-urea,

(24) 1-{2-(4-Morpholino)-5-[2-(3-ethyl-4-methyl-2-oxo-3-pyrrolinyl-1-carboxamido)-ethyl]-phenylsulfonyl-}3-(cyclopropyl)-urea,

(25) 1-{2-Methyl-5-[2-(3-ethyl-4-methyl-2-oxo-3-pyrrolinyl-1-carboxamido)-ethyl]-phenylsulfonyl-}3-ethylurea,

(26) 1-{2-Methyl-5-[2-(3-ethyl-4-methyl-2-oxo-3-pyrrolinyl-1-carboxamido)-ethyl]-phenylsulfonyl-}3-(1-propyl)-urea,

(27) 1-{2-Methyl-5-[2-(3-ethyl-4-methyl-2-oxo-3-pyrrolinyl-1-carboxamido)-ethyl]-phenylsulfonyl-}3-(2-propyl)-urea,

(28) 1-{2-Methyl-5-[2-(3-ethyl-4-methyl-2-oxo-3-pyrrolinyl-1-carboxamido)-ethyl]-phenylsulfonyl-}3-(cyclopropyl)-urea

(29) 1-{2-Fluoro-5-[2-(3-ethyl-4-methyl-2-oxo-3-pyrrolinyl-1-carboxamido)-ethyl]-phenylsulfonyl-}3-ethylurea,

(30) 1-{2-Fluoro-5-[2-(3-ethyl-4-methyl-2-oxo-3-pyrrolinyl-1-carboxamido)-ethyl]-phenylsulfonyl-}3-(1-propyl)-urea,

(31) 1-{2-Fluoro-5-[2-(3-ethyl-4-methyl-2-oxo-3-pyrrolinyl-1-carboxamido)-ethyl]-phenylsulfonyl-}3-(2-propyl)-urea,

(32) 1-{2-Fluoro-5-[2-(3-ethyl-4-methyl-2-oxo-3-pyrrolinyl-1-carboxamido)-ethyl]-phenylsulfonyl-}3-(cyclopropyl)-urea,

(33) 1-{2-Methoxy-5-[2-(3-ethyl-4-methyl-2-oxo-3-pyrrolinyl-1-carboxamido)-ethyl]-phenylsulfonyl-}3-ethylthiourea,

(34) 1-{2-Methoxy-5-[2-(3-ethyl-4-methyl-2-oxo-3-pyrrolinyl-1-carboxamido)-ethyl]-phenylsulfonyl-}3-(1-propyl)-thiourea,

(35) 1-{2-Methoxy-5-[2-(3-ethyl-4-methyl-2-oxo-3-pyrrolinyl-1-carboxamido)-ethyl]-phenylsulfonyl-}3-(1-propyl)-thiourea,

(36) 1-{2-Methoxy-5-[2-(3-ethyl-4-methyl-2-oxo-3-pyrrolinyl-1-carboxamido)-ethyl]-phenylsulfonyl-}3-(2-propyl)-thiourea,

(37) 1-{2-Methoxy-5-[2-(3-ethyl-4-methyl-2-oxo-3-pyrrolinyl-1-carboxamido)-ethyl]-phenylsulfonyl-}3-(cyclopropyl)-thiourea,

(38) 1-{2-Ethoxy-5-[2-(3-ethyl-4-methyl-2-oxo-3-pyrrolinyl-1-carboxamido)-ethyl]-phenylsulfonyl-}3-ethylthiourea,

(39) 1-{2-Ethoxy-5-[2-(3-ethyl-4-methyl-2-oxo-3-pyrrolinyl-1-carboxamido)-ethyl]-phenylsulfonyl-}3-(1-propyl)-thiourea,

(40) 1-{2-Ethoxy-5-[2-(3-ethyl-4-methyl-2-oxo-3-pyrrolinyl-1-carboxamido)-ethyl]-phenylsulfonyl-}3-(2-propyl)-thiourea,

(41) 1-{2-Ethoxy-5-[2-(3-ethyl-4-methyl-2-oxo-3-pyrrolinyl-1-carboxamido)-ethyl]-phenylsulfonyl-}3-(cyclopropyl)-thiourea,

(42) 1-{2-(2,2,2-Trifluoroethoxy)-5-[2-(3-ethyl-4-methyl-2-oxo-3-pyrrolinyl-1-carboxamido)-ethyl]-phenylsulfonyl-}3-ethylthiourea,

(43) 1-{2-(2,2,2-Trifluoroethoxy)-5-[2-(3-ethyl-4-methyl-2-oxo-3-pyrrolinyl-1-carboxamido)-ethyl]-phenylsulfonyl-}3-(1-propyl)-thiourea,

(44) 1-{2-(2,2,2-Trifluoroethoxy)-5-[2-(3-ethyl-4-methyl-2-oxo-3-pyrrolinyl-1-carboxamido)-ethyl]-phenylsulfonyl-}3-(2-propyl)-thiourea,

(45) 1-{2-(2,2,2-Trifluoroethoxy)-5-[2-(3-ethyl-4-methyl-2-oxo-3-pyrrolinyl-1-carboxamido)-ethyl]-phenylsulfonyl-}3-(cyclopropyl)-thiourea,

(46) 1-{2-Thiomethyl-5-[2-(3-ethyl-4-methyl-2-oxo-3-pyrrolinyl-1-carboxamido)-ethyl]-phenylsulfonyl-}3-ethylthiourea,

(47) 1-{2-Thiomethyl-5-[2-(3-ethyl-4-methyl-2-oxo-3-pyrrolinyl-1-carboxamido)-ethyl]-phenylsulfonyl-}3-(1-propyl)-thiourea,

(48) 1-{2-Thiomethyl-5-[2-(3-ethyl-4-methyl-2-oxo-3-pyrrolinyl-1-carboxamido)-ethyl]-phenylsulfonyl-}3-(2-propyl)-thiourea,

(49) 1-{2-Thiomethyl-5-[2-(3-ethyl-4-methyl-2-oxo-3-pyrrolinyl-1-carboxamido)-ethyl]-phenylsulfonyl-}3-(cyclopropyl)-thiourea,

(50) 1-{2-(N,N-dimethylamino)-5-[2-(3-ethyl-4-methyl-2-oxo-3-pyrrolinyl-1-carboxamido)-ethyl]-phenylsulfonyl-}3-ethylthiourea,

(51) 1-{2-(N,N-dimethylamino)-5-[2-(3-ethyl-4-methyl-2-oxo-3-pyrrolinyl-1-carboxamido)-ethyl]-phenylsulfonyl-}3-(1-propyl)-thiourea,

(52) 1-{2-(N,N-dimethylamino)-5-[2-(3-ethyl-4-methyl-2-oxo-3-pyrrolinyl-1-carboxamido)-ethyl]-phenylsulfonyl-}3-(2-propyl)-thiourea,

(53) 1-{2-(N,N-dimethylamino)-5-[2-(3-ethyl-4-methyl-2-oxo-3-pyrrolinyl-1-carboxamido)-ethyl]-phenylsulfonyl-}3-(cyclopropyl)-thiourea,

(54) 1-{2-(4-Morpholino)-5-[2-(3-ethyl-4-methyl-2-oxo-3-pyrrolinyl-1-carboxamido)-ethyl]-phenylsulfonyl-}-3-ethylthiourea,

(55) 1-{2-(4-Morpholino)-5-[2-(3-ethyl-4-methyl-2-oxo-3-pyrrolinyl-1-carboxamido)-ethyl]-phenylsulfonyl-}-3-(1-propyl)-thiourea,

(56) 1-{2-(4-Morpholino)-5-[2-(3-ethyl-4-methyl-2-oxo-3-pyrrolinyl-1-carboxamido)-ethyl]-phenylsulfonyl-}-3-(2-propyl)-thiourea,

(57) 1-{2-(4-Morpholino)-5-[2-(3-ethyl-4-methyl-2-oxo-3-pyrrolinyl-1-carboxamido)-ethyl]-phenylsulfonyl-}-3-(cyclopropyl)-thiourea,

(58) 1-{2-Methyl-5-[2-(3-ethyl-4-methyl-2-oxo-3-pyrrolinyl-1-carboxamido)-ethyl]-phenylsulfonyl-}3-ethylthiourea,

(59) 1-{2-Methyl-5-[2-(3-ethyl-4-methyl-2-oxo-3-pyrrolinyl-1-carboxamido)-ethyl]-phenylsulfonyl-}3-(1-propyl)-thiourea,

(60) 1-{2-Methyl-5-[2-(3-ethyl-4-methyl-2-oxo-3-pyrrolinyl-1-carboxamido)-ethyl]-phenylsulfonyl-}3-(2-propyl)-thiourea,
(61) 1-{2-Methyl-5-[2-(3-ethyl-4-methyl-2-oxo-3-pyrrolinyl-1-carboxamido)-ethyl]-phenylsulfonyl-}3-(cyclopropyl)-thiourea,
(62) 1-{2-Fluoro-5-[2-(3-ethyl-A-methyl-2-oxo-3-pyrrolinyl-1-carboxamido)-ethyl]-phenylsulfonyl-}3-ethylthiourea,
(63) 1-{2-Fluoro-5-[2-(3-ethyl-4-methyl-2-oxo-3-pyrrolinyl-1-carboxamido)-ethyl]-phenylsulfonyl-}3-(1-propyl)-thiourea,
(64) 1-{2-Fluoro-5-[2-(3-ethyl-4-methyl-2-oxo-3-pyrrolinyl-1-carboxamido)-ethyl]-phenylsulfonyl-}3-(2-propyl)-thiourea,
(65) 1-{2-Fluoro-5-[2-(3-ethyl-4-methyl-2-oxo-3-pyrrolinyl-1-carboxamido)-ethyl]-phenylsulfonyl-}3-(cyclopropyl)-thiourea, 1-Oxo-3,4-dihydroisoquinolinyl-2-carboxamides
(66) N-{5-[Sulfonylamino-N-(methylaminocarbonyl)-2-methoxyphenyl]-ethyl}-1-oxo-3,4-dihydroisoquinolinyl-2-carboxamide,
(67) N-{5-[Sulfonylamino-N-(methylaminothiocarbonyl)-2-methoxyphenyl]-ethyl}-1-oxo-3,4-dihydroisoquinolinyl-2-carboxamide,
(68) N-{5-[Sulfonylamino-N-(methylaminocarbonyl)-2-methoxyphenyl]-ethyl}-1-oxo-3,4-dihydroisoquinolinyl-2-carboxamide,
(69) N-{5-[Sulfonylamino-N-(methylaminothiocarbonyl)-2-methylphenyl]-ethyl}-1-oxo-3,4-dihydroisoquinolinyl-2-carboxamide, 1-Oxo-3H-isoindolinyl-2-carboxamides
(70) N-{5-[Sulfonylamino-N-(methylaminocarbonyl)-2-methoxyphenyl]-ethyl}-1-oxo-3H-isoindolinyl-2-carboxamide,
(71) N-{5-[Sulfonylamino-N-(methylaminothiocarbonyl)-2-methoxyphenyl]-ethyl}-1-oxo-3H-isoindolinyl-2-carboxamide,
(72) N-{5-[Sulfonylamino-N-(methylaminocarbonyl)-2-methylphenyl]-ethyl}-1-oxo-3H-isoindolinyl-2-carboxamide,
(73) N-{5-[Sulfonylamino-N-(methylaminothiocarbonyl)-2-methylphenyl]-ethyl}-1-oxo-3H-isoindolinyl-2-carboxamide.

EXAMPLE 1

1-{2-Methoxy-5-[2-(3-ethyl-4-methyl-2-oxo-3-pyrrolinyl-1-carboxamido)-ethyl]-phenylsulfonyl-}3-methylthiourea

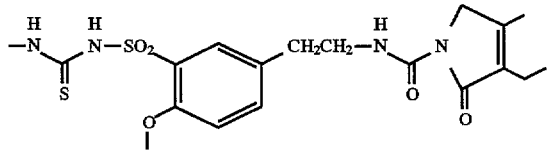

0.22 g (0.58 mmol) of 2-methoxy-5-[2-(3-ethyl-4-methyl-2-oxo-3-pyrrolinyl-1-carboxamido)-ethyl]-benzenesulfomamide are dissolved in 10 ml of acetone, and 25 mg of NaOH and 50 μl of water are added. 45 mg (0.6 mmol) of methylisothiocyanate are added to the well-stirred reaction mixture, while cooling in ice, the mixture is subsequently stirred at room temperature for one hour and the solvent is then removed under reduced pressure. The residue which reins is purified by column chromatography over silica gel 60 with the aid of the mobile phase ethyl acetate ($R_f$=0.4) and gives 0.18 g of the desired product as colorless crystals which melt at 65° to 70° C.

Preparation of the starting compound 4.53 g (30 mol) of 4-methoxy-β-phenylethylamine are added dropwise to a solution of 2.96 g (10.0 mol) of triphosgene in 30 ml of dry tetrahydrofuran and the mixture is heated at the boiling point for 2 hours. The solution is cooled to room temperature and filtered and the filtrate is concentrated in vacuo. The colorless oil which remains is purified by bulb tube distillation under a pressure of 2 mmHg at a bath temperature of 220° C. to give 1.1 g of 4-methoxy-β-phenylethyl isocyanate. 0.7 g (4.0 mmol) of 4-methoxy-β-phenylethyl isocyanate and 0.4 g (3.5 mmol) of 3-ethyl-4-methyl-2-oxo-3-pyrroline are stirred with one another and the mixture is heated at 150° C. for one hour. The cooled reaction mixture is dissolved in a minimum of ethyl acetate and purified by column chromatography over silica gel 60 with the aid of the mobile phase ethyl acetate ($R_f$=0.5). After the eluent has been evaporated off under reduced pressure, 0.25 g of methoxy-4-[2-(3-ethyl-4-methyl-2-oxo-3-pyrrolinyl-1-carboxamido)-ethyl]-benzene is obtained, and is introduced in portions into chlorosulfonic acid cooled to 0° C. After being stirred at 0° C. for one hour, this reaction mixture is poured onto ice. The sulfonic acid chloride which has precipitated is taken up in ethyl acetate. The organic phase is dried with sodium sulfate and concentrated in vacuo to give the sulfonic acid chloride as a crude product, which is dissolved in acetone and converted into 2-methoxy-5-[2-(3-ethyl-4-methyl-2-oxo-3-pyrrolinyl-1-carboxamido)-ethyl]-benzenesulfonamide with aqueous ammonia solution. The sulfonamide has a melting point of 204°–205° C.

EXAMPLE 2

1-{2-Methoxy-5-[2-(3-ethyl-4-methyl-2-oxo-3-pyrrolinyl-1-carboxamido)-ethyl]-phenylsulfonyl-}3-methylurea

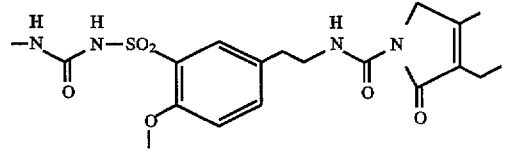

0.25 g (0.55 mmol) of 1-{2-methoxy-5-[2-(3-ethyl-4-methyl-2-oxo-3-pyrrolinyl-1-carboxamido)-ethyl]-phenylsulfonyl}3-methylthiourea is suspended in aqueous sodium hydroxide solution (45 mg of NaOH and 0.5 ml of water), 35% strength aqueous hydrogen peroxide is added at 40° C. and the mixture is subsequently stirred at 80° C. for 30 minutes. Methylene chloride is added to the reaction mixture at room temperature and the mixture is acidified with a little 2 normal aqueous hydrochloric acid (pH=2–3) and dried with sodium sulfate. The organic phase is concentrated in vacuo to give 0.22 g of 1-{2-methoxy-5-[2-(3-ethyl-4-methyl-2-oxo-3-pyrrolinyl-1-carboxamido)-ethyl]-phenylsulfonyl-}3-methylurea as colorless crystals of melting point 184°–187° C.

EXAMPLE 3

1-{2-Fluoro-5-[2-(3-ethyl-4-methyl-2-oxo-3-pyrrolinyl-1-carboxamido)-ethyl]-phenylsulfonyl-}-3-methylthiourea

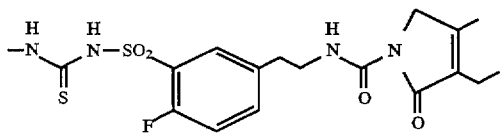

In accordance with Exmaple 1, 1-{2-fluoro-5-[2-(3-ethyl-4-methyl-2-oxo-3-pyrrolinyl-1-carboxamido)-ethyl]-phenylsulfonyl-}3-methylthiourea (melting point: 90° C., with decomposition) can be synthesized starting from 4-fluoro-β-phenylethylamine via fluoro-4-[2-(3-ethyl-4-methyl-2-oxo-3-pyrrolinyl-1-carboxamido)-ethyl]-benzene (melting point: 141° C.), 2-fluoro-5-[2-(3-ethyl-β-methyl-2-oxo-3-pyrrolinyl-1-carboxamido)-ethyl]-benzenesulfonyl chloride (melting point: 147° C.) and 2-fluoro-5-[2-(3-ethyl-4-methyl-2-oxo-3-pyrrolinyl-1-carboxamido)-ethyl]-benzenesulfonamide (melting point: 136° C.).

EXAMPLE 4

1-[2-Ethoxy-5-[2(3-ethyl-4-methyl-2-oxo-3-pyrrolinyl-1-carboxamido)-ethyl]-phenylsulfonyl]-3-methylthiourea Melting point 176°–178° C.

Analogously to Example 1

EXAMPLE 5

1-[2-Ethoxy-5-[2-(3-ethyl-4-methyl-2-oxo-3-pyrrolinyl-1-carboxamido)-ethyl]-phenylsulfonyl]-3-methylurea Melting point: 160°–165° C.

Analogously to Example 2

Pharmacological data:

The therapeutic properties of the compounds I can be demonstrated using the following models:

(1) Action potential duration on the papillary muscle of the guineapig:

(a) Introduction

ATP deficiency states such as are observed during ischemia in the cardiac muscle cell lead to a shortening of the duration of action potential. They are one of the causes of so-called reentry arrhythmias, which can cause sudden cardiac death. Opening of ATP-sensitive K by the reduction in ATP is a cause of this.

(b) Method

A standard microelectrode technique is used for measurement of the action potential. For this, guineapigs of both sexes are sacrificed by a blow to the head, the hearts are removed and the papillary muscles are separated out and suspended in an organ bath. The organ bath is flushed with Ringer solution (0.9% NaCl, 0.048% KCl, 0.024% $CaCl_2$, 0.02% $NaHCO_3$ and 0.1% glucose) and gassed with a mixture of 95% oxygen and 5% carbon dioxide at a temperature of 36° C. The muscle is stimulated via an electrode with rectangular pulses of 1 V and 1 ms duration and a frequency of 2 Hz. The action potential is conducted and recorded through a glass microelectrode, which is punctured intracellularly and filled with 3 mmol KCl solution. The substances to be tested were added to the Ringer solution in a concentration of $2.2 \times 10^{-5}$ mol per liter. The action potential is shown in amplified form on an oscilloscope using a Hugo Sachs amplifier. The duration of the action potential is determined at a repolarization degree of 95% ($APD_{95}$). Shortenings in action potential are caused either by addition of a 1 µM strength solution of the potassium channel opener rilmakalim (Hoe 234) [W. Linz, E. Klaus, U. Albus, R. H. A. Becker, D. Mania, H. C. Englert, B. A. Schölkens Arzneimittelforschung/ Drug Research, Volume 42 (II), 1992, pages 1180–1185] or by addition of 2-deoxyglucose (DEO). ATP deficiency states are caused in experimental physiology by 2-deoxyglucose by blockade of glucose metabolism. The action potential-shortening effect of these substances was prevented or reduced by the simultaneous dose of the test substances. The test substances were added to the bath solution as stock solutions in propanediol. The values stated relate to measurements 30 minutes after the addition. The $APD_{95}$ in the presence of DEO or HOE 234 and in the absence of the test substance serves as a control.

(c) Results:

The following values were measured:

| Measurement | $APD_{95}$-DEO[a] [ms] | $APD_{95}$-HOE 234[a] [ms] |
|---|---|---|
| Control | <40 | <40 |
| Example 1 | 60 ± 22 | 119 ± 16 |
|  | (162 ± 7) | (162 ± 16) |
|  | n = 3 | n = 3 |
| Example 2 | 110 (155) | 125 (185) |
|  | n = 1 | n = 1 |

[a] The measurement values from n experiments are followed by the corresponding blank values in parentheses. The blank values are the $APD_{95}$ values at the start of the experiment without DEO, HOE 234 or test substance in the Ringer solution.

(2) Membrane potential on isolated β cells:

(a) Introduction

The action mechanism of hypoglycemic sulfonylureas is clarified in rough outlines. The β cells of the pancreas are the target organ, where increased secretion of the hypoglycamic hormone insulin occurs. The release of insulin is controlled by the cell membrane potential. Glibenclamide causes depolarization of the cell membrane, which promotes insulin release via an increased in-flow of calcium ions. The extent of this depolarization of the cell membrane ΔU was determined on RINm5F cells, a pancreas tumor cell line, for some of the compounds according to the invention. The action strength of a compound in this model predicts the extent of the hypoglycemic potential of this compound.

(b) Method

Cell culture of RINm5F cells

RINm5F cells were cultured at 37° C. in RPMI 1640 culture medium (flow), to which 11 mmol of glucose, 10% (volume/volume) of fetal calf serum, 2 mmol of glutamine and 50 µg/ml of gentamycin were added. For the studies, the cells were isolated by incubation (about 3 minutes) in a $Ca^{2+}$-free medium containing 0.25% of trypsin and stored on ice.

Measurement method

Isolated RINm5F cells were introduced into a Plexiglas., chamber on an inverse microscope fitted with a differential interference contrast lens. A fire-polished micropipette pipette with an opening diameter of about 1 µm was placed on the cell with the aid of a micro-manipulator under optical control (400-fold magnification). By applying a slight reduced pressure in the patch pipette, a high electrical seal was first produced between the glass and cell membrane, and was then broken open by increasing the reduced pressure of the membrane spot under the measurement pipette. The cell potential was recorded in this whole cell configuration with the aid of a patch clamp amplifier (L/M EPC 7) and was measured by applying a potential ramp to the whole cell current.

Solutions: The patch pipette was filled with KCl solution (in mmol): 140 KCl, 10 NaCl, 1.1 $MgCl_2$, 0.5 EGTA, 1 Mg-ATP, 10 HEPES, pH=7.2, and the bath contained NaCl solution (in mmol): 140 NaCl, 4.7 KCl, 1.1 $MgCl_2$, 2 $CaCl_2$, 10 HEPES, pH=7.4. Stock solutions of the test substances (concentration 100 mmol) in dimethyl sulfoxide (DMSO) and corresponding dilutions in NaCl solution were prepared. DMSO by itself had no effect on the cell potential. In order to stabilize the cell potential under control conditions, the opener for ATP-sensitive K⁺ channels diazoxide (100 µmol) was added to the bath solution in all the experiments. All the experiments were carried out at 34°±1° C.

(c) Results (The concentrations of the compounds according to the invention in the experiments are $10^{-5}$ mol per liter)

| Measurement | ΔU (mV)[a] |
|---|---|
| Example 1 | 2 (−80) n = 6 |
| Example 2 | 12 (−71) n = 6 |

[a] The measurement values from n experiments are followed by the corresponding blank values in parentheses. The blank values are the cell potentials under a dose of diazoxide.

We claim:
1. A substituted benzenesulfonylurea or -thiourea of the formula I

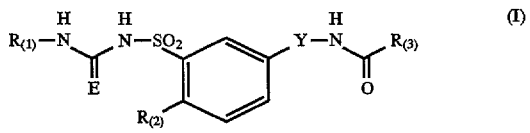

in which:
R(1) is hydrogen, $(C_1-C_4)$-alkyl, $(C_3-C_4)$-cycloalkyl, $(C_3-C_4)$-alkenyl or $(C_1-C_4)$-fluoroalkyl;
R(2) is $(C_1-C_4)$-alkoxy, $(C_1-C_4)$-mercaptoalkyl, or $(C_1-C_4)$-fluoroalkoxy;
E is oxygen or sulfur;
Y is a hydrocarbon chain —{CR(7)$_2$}$_n$—;
R(7) is H or $(C_1-C_2)$-alkyl;
n is 2 or 3;
R(3) is a bicyclic system of the formula

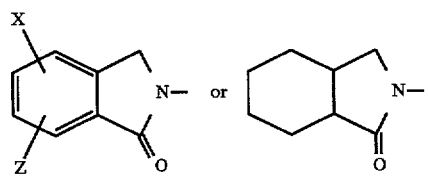

X is hydrogen, F, Cl or $(C_1-C_3)$-alkyl;
Z is hydrogen, F, Cl or $(C_1-C_4)$-alkoxy,
or a physiologically acceptable salt thereof.

2. A substituted benzenesulfonylurea or -thiourea of the formula

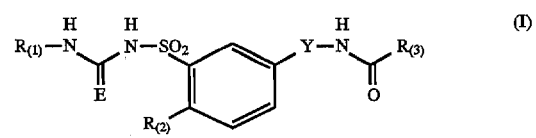

in which:
R(1) is hydrogen, $(C_1-C_4)$-alkyl, $(C_3-C_4)$-alkenyl or $(C_1-C_4)$-fluoroalkyl;
R(2) is NR(4)R(5);
R(4) and R(5)
together are a $(CH_2)$4-6 chain in which one of the $CH_2$ groups may be replaced by oxygen, sulfur, or NR(6) where at least one $CH_2$ group must stand between the N atom of the NR(4)R(5) and the oxygen, sulfur, or NR(6);

or
R(4) and R(5) independently of one another are $CH_3$, $C_2H_5$, n-$C_3H_7$, iso-$C_3H_7$ or cyclo-$C_3H_5$;
R(6) is H, $CH_3$ or $C_2H_5$;
E is oxygen or sulfur;
Y is a hydrocarbon chain —{CR(7)$_2$}$_n$—;
R(7) is H or $(C_1-C_2)$-alkyl;
n is 2 or 3;
R(3) is a bicyclic system of the formula

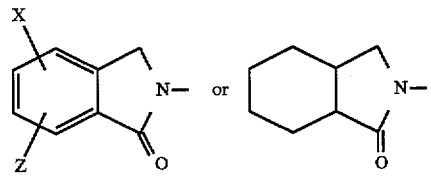

X is hydrogen, F, Cl or $(C_1-C_3)$-alkyl;
Z is hydrogen, F, Cl, or $(C_1-C_4)$-alkoxy,
or a physiologically acceptable salt thereof.

3. A compound of the formula (I) as claimed in claim 1, in which:
R(1) is methyl,
R(2) is methoxy,
E is sulfur,
Y is —$CH_2$—$CH_2$—, and
R(3) is:

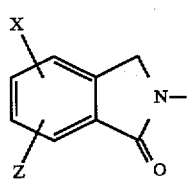

where X is hydrogen and Z is fluorine, or a physiologically acceptable salt thereof.

4. N-{5[Sulfonylamino-N-(methylaminocarbonyl-2-methoxyphenyl]-ethyl}-1-oxo-3H-isoindolinyl-2-carboxamide or a physiologically acceptable salt thereof.

5. N-{5-[Sulfonylamino-N-(methylaminothiocarbonyl)-2-methoxyphenyl]-ethyl}-1-oxo-3H-isoindolinyl-2-carboxamide or a physiologically acceptable salt thereof.

6. N-{5-[Sulfonylamino-N-(methylaminothiocarbonyl)-2-methylphenyl]-ethyl}-1-oxo-3H-isoindolinyl-2-carboxamide or a physiologically acceptable salt thereof.

7. A pharmaceutical composition comprising an effective amount of a compound of the formula I as claimed in claim 1 or a physiologically acceptable salt thereof and a pharmaceutically acceptable excipient or auxiliary.

8. A pharmaceutical composition comprising an effective amount of a compound of the formula I as claimed in claim 2 or a physiologically acceptable salt thereof and a pharmaceutically acceptable excipient or auxiliary.

9. A method for the treatment of disturbances in cardiac rhythm comprising administering to a human or animal patient in need thereof an effective amount of at least one compound of formula I of claim 1, or a physiologically acceptable salt thereof.

10. A method for the treatment of ischemic conditions of the heart comprising administering to a human or animal patient in need thereof an effective amount of at least one compound of formula I of claim 1, or a physiologically acceptable salt thereof.

11. A method for the treatment of disturbances in cardiac rhythm comprising administering to a human or animal patient in need thereof an effective amount of at least one compound of formula I of claim 2 or a physiologically salt thereof.

12. A method for the treatment of ischemic conditions of the heart comprising administering to a human or animal patient in need thereof an effective amount of at least one compound of formula I of claim 2 or a physiologically acceptable salt thereof.

* * * * *

UNITED STATES PATENT AND TRADEMARK OFFICE
CERTIFICATE OF CORRECTION

PATENT NO. : 5,731,341
DATED : March 24, 1998
INVENTOR(S) : ENGLERT et al.

It is certified that error appears in the above-indentified patent and that said Letters Patent is hereby corrected as shown below:

Claim 2, column 21, line 50, after "formula", insert --I--.

Claim 2, column 21, line 63, "(CH$_2$)4-6" should read --(CH$_2$)$_{4-6}$--.

Claim 4, column 22, line 41, after "(methylaminocarbonyl", insert --)--.

Claim 11, column 23, line 4, after "physiologically", insert --acceptable--.

Signed and Sealed this

Twenty-fifth Day of May, 1999

Attest:

Q. TODD DICKINSON

Attesting Officer     Acting Commissioner of Patents and Trademarks